US008750963B2

(12) United States Patent
Doerr et al.

(10) Patent No.: US 8,750,963 B2
(45) Date of Patent: Jun. 10, 2014

(54) IMPLANTABLE DEVICE

(75) Inventors: Thomas Doerr, Berlin (DE); Ingo Weiss, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 219 days.

(21) Appl. No.: 13/418,326

(22) Filed: Mar. 12, 2012

(65) Prior Publication Data
US 2012/0245452 A1 Sep. 27, 2012

Related U.S. Application Data

(60) Provisional application No. 61/466,486, filed on Mar. 23, 2011.

(51) Int. Cl.
*A61B 5/055* (2006.01)
*A61N 1/02* (2006.01)
*A61N 1/37* (2006.01)
*A61N 1/372* (2006.01)

(52) U.S. Cl.
CPC *A61N 1/025* (2013.01); *A61N 1/37* (2013.01); *A61N 1/3718* (2013.01); *A61N 1/37282* (2013.01); *A61B 2560/063* (2013.01); *A61B 2560/066* (2013.01)
USPC ............ 600/411; 607/17; 607/18; 607/30

(58) Field of Classification Search
CPC ....... A61N 1/025; A61N 1/37; A61N 1/3718; A61N 1/37282; A61B 2560/063; A61B 2560/066
USPC ............ 600/407, 411, 374; 607/9, 30, 37, 63, 607/17, 18
See application file for complete search history.

(56) References Cited

U.S. PATENT DOCUMENTS

| 7,369,898 | B1 | 5/2008 | Kroll et al. |
| 2009/0210025 | A1 | 8/2009 | Ameri |
| 2010/0106212 | A1* | 4/2010 | Hedberg et al. ................ 607/18 |
| 2010/0106215 | A1* | 4/2010 | Stubbs et al. .................. 607/37 |
| 2010/0152806 | A1* | 6/2010 | Levine et al. .................. 607/30 |
| 2011/0152672 | A1 | 6/2011 | Doerr |
| 2011/0152673 | A1 | 6/2011 | Doerr |
| 2012/0158079 | A1* | 6/2012 | Rosenberg et al. ............. 607/9 |
| 2012/0220849 | A1* | 8/2012 | Brockway et al. ........... 600/374 |
| 2013/0012800 | A1* | 1/2013 | Brockway et al. ........... 600/374 |

FOREIGN PATENT DOCUMENTS

| EP | 2198914 A1 | 6/2010 |
| WO | 98/33554 A1 | 8/1998 |
| WO | 2007013917 A1 | 2/2007 |

OTHER PUBLICATIONS

European Search Report dated Aug. 16, 2012, 6 pages.
European Search Report dated Nov. 21, 2012, 11 pages.

* cited by examiner

*Primary Examiner* — Baisakhi Roy
(74) *Attorney, Agent, or Firm* — ARC IP Law, PC; Joseph J. Mayo

(57) ABSTRACT

An implantable electromedical device, having a detection unit for capturing possible device-impairing effects, a control unit, which is connected to the detection unit, a diagnostic and/or treatment unit, and a test unit, of which the test unit is designed to test the diagnostic-treatment unit, and to output test results for storage, of which the diagnostic and/or treatment unit includes sensor units and/or treatment delivery units as components and is designed to record physiological parameters and/or bring about delivery of a treatment, and of which the control unit is designed to actuate the test unit for testing the diagnostic-treatment unit.

15 Claims, 5 Drawing Sheets

IMPLANTABLE DEVICE

This application claims the benefit of U.S. Provisional Patent Application 61/466,486, filed on 23 Mar. 2011, the specification of which is hereby incorporated herein by reference.

BACKGROUND OF THE INVENTION

1. Field of the Invention

The present disclosure is related to an implantable electromedical device.

2. Description of the Related Art

Implantable cardiac pacemakers or defibrillators are typically connected to electrode lines for electrostimulation, which are associated with the disadvantage that the electric conductor can heat up in a nuclear magnetic resonance tomograph (also referred to as magnetic resonance imaging scanner or MRI scanner) because the alternating magnetic fields present in the nuclear magnetic resonance tomograph induce quite significant electrical currents in the electric conductor. Such induced currents can also be delivered to surrounding tissue by electrode poles of the electrode line and thus result in undesirable heating of tissue, for example. Induced currents could also impair or damage components of the device, or electric resistance between the potential-capturing or pulse-delivering electrode poles could change, such as increased, at the electrode line. This impairs the capturing or evaluation of electric signals of a heart and thus can impair the control of the treatment, or the delivery of the treatment. For this reason, cardiac pacemaker patients today cannot be examined with nuclear magnetic resonance tomographs, or only to a limited extent.

Typically, implantable cardiac pacemakers or defibrillators (hereinafter jointly referred to as cardiac stimulators or implantable pulse generators (IPG)) are connected at least to such an electrode line that comprises a standardized electrical connection at the proximal end thereof provided for connection to the cardiac pacemaker or defibrillator and one or more electrode poles at the distal end thereof provided for placement in the heart. Such an electrode pole is used to deliver electric pulses to the tissue (myocardium) of the heart or to sense electric fields, so as to be able to sense an activity of a heart as part of the sensing process. For these purposes, electrode poles typically form electrically conductive surface sections of an electrode line. Electrode poles are typically provided as annular electrodes in the form of a ring around the electrode line, or in the form of tip electrodes, at the distal end of the electrode line. The electrode poles are electrically conductively connected to contacts of the electric connection of the electrode line at the proximal end by way of one or more electric conductors. In this way, one or more electric conductors, which electrically connect one or more of the electrode poles to one or more of the contacts, run between the contacts of the electric connection of the electrode lines at the proximal end and the electrode poles at the distal end of the electrode line. The electric conductors can be used both to transmit stimulation pulses to the electrode poles and to transmit electric signals picked up by the electrode poles to the proximal end of the electrode line.

BRIEF SUMMARY OF THE INVENTION

An objective of one or more embodiments of the invention is to implement a safe MRI examination of patients with electronic implants.

This objective is achieved by an implantable electromedical device, comprising
- an MRI detection unit for capturing MRI-typical magnetic fields and/or alternating electromagnetic fields and/or mechanical oscillations,
- a control unit, which is connected to the MRI detection unit
- a diagnostic-treatment unit, comprising at least a diagnostic unit or a treatment unit or both (hereinafter referred to in short as diagnostic-treatment unit) and
- a test unit.

The test unit is designed to test the diagnostic-treatment unit or components of the diagnostic-treatment unit and to output test results obtained in this way, for example to a storage unit, for storage. The diagnostic-treatment unit comprises sensor units and/or treatment delivery units as components and is designed to record physiological parameters and/or cause delivery of a treatment. The control unit is designed to actuate the test unit so as to test the diagnostic-treatment unit. According to one or more embodiments of the invention, the control unit is connected to the MRI detection unit and designed to trigger a before-test of at least one component of the diagnostic-treatment unit by the test unit in response to an output signal indicating an MRI-typical magnetic field and/or alternating electromagnetic field and/or mechanical vibrations, wherein during the before-test the test unit captures values of system integrity parameters that characterize an operating capability of the implantable medical device. Such implantable medical devices are, for example, implantable defibrillators (ICDs) or cardiac pacemakers, which can deliver electric stimulation pulses to the heart tissue (myocardium) by way of electrode lines or capture electric potentials in the heart tissue by way of suitable sensors. Other implants, such as neurostimulators, are used to stimulate other tissue. In connection with cardiac pacemakers, it is known that they independently carry out automatic after-care, referred to as "cron jobs", which is to say preprogrammed self-tests in terms of the sequence and time, wherein defined parameters are captured, for example the stimulus threshold, electrode impedance, battery voltage, signal amplitudes, etc., as is customary according to current guidelines. For this purpose, the test unit actuated by the control unit is used.

As mentioned above, the MRI detection unit can comprise an MRI sensor, as that which is known from United States Patent Application Publication No. 20110152672, for example. The diagnostic-treatment unit can be a pure diagnostic unit, or a pure treatment unit, for example a stimulation unit of a cardiac pacemaker, or a combination of both. The diagnostic unit can be a sensing unit, for example, which is known from cardiac pacemakers, for capturing and optionally evaluating electric potentials indicating cardiac events.

The implantable medical device according to one or more embodiments of the invention is able to independently detect MRI-typical (and similar) magnetic fields and/or alternating electromagnetic fields and/or mechanical oscillations, and thereupon values of important system integrity parameters characterizing an operating capability of the implantable medical device, whereby it creates the prerequisites for detecting a change in these values as a result of the action of such fields on the device.

Until now, the MRI examination was contraindicated in patients with electronic implants, such as cardiac pacemakers, ICDs, CRT-Ds or neurostimulators, because problems, such as the heating of the electrode tip, can occur in the surroundings of the MRI because of the strong alternating electromagnetic fields in the MRI. In particular the heating of the electrode tip can result in a temporary or permanent increase in the stimulus threshold, undersensing or oversensing, or even dislocation. The latter can be independently captured by the device according to one or more embodiments of the invention and thus allows, for example, an implant and electrode system to be checked after an MRI examination has been carried out, so as to detect system errors of the electronic implant and MRI-induced electrode problems.

For a follow-up examination required after an MRI procedure, until now an implant specialist (for example a cardiologist/electrophysiologist) was required to carry out the examination. The MRI, however, is typically carried out by radiologists, who are not trained and not authorized to check the implant functions of an electronic implant. The patient therefore typically must visit a second medical specialist before, and in particular after, the MRI examination. This considerably increases the costs for the MRI procedure and has the inherent risk that the subsequent examination does not take place. The device according to one or more embodiments of the invention makes such a prior examination by a medical specialist before an MRI procedure superfluous.

Compared to a "normal" MRI procedure, the overall procedure includes two additional procedures by an implant specialist and requires the implant specialist and radiologist to work closely with each other, both temporally and spatially, which in practical experience can only be implemented with considerably increased expenditure.

The implantable electromedical device is preferably designed to detect an discontinuation of an output signal of the MRI detection unit that indicates an MRI-typical magnetic field and/or alternating electromagnetic field and/or mechanical vibrations, and to then have the test unit trigger an after-test, preferably of the component of the diagnostic-treatment unit for which a before-test was carried out, and during which preferably values of those system integrity parameters are captured for which values are available from the before-test. Such an implantable electromedical device also makes a local follow-up examination, for example by a cardiologist, superfluous or at least facilitates the same. Values captured for the implantable electromedical device during the before-test and after-test can be transmitted telemetrically to a central service center and be evaluated there, either automatically or by a physician.

The control unit is preferably designed to switch the implantable medical device, subsequent to an after-test, into a post-MRI operating mode, in which after-tests are carried out cyclically, wherein the control unit is further designed to compare values of a particular system integrity parameter from a particular after-test to a corresponding value of the same system integrity parameter from the last before-test. In this way, the implantable medical device can autonomously detect potentially critical changes in values of the system integrity parameters.

In addition, the control unit is preferably designed to terminate the post-MRI operating mode when a deviation of the values takes place beneath a specified threshold value.

If the implantable electromedical device is a stimulator or a monitoring implant comprising a tissue-contacting electrode pole, or a terminal for a tissue-contacting electrode pole, the system integrity parameter, or one of the system integrity parameters, is preferably an impedance value characterizing an electrode-tissue contact. This preferred variant is based on the realization that the impedance value can dramatically change between an electrode pole and adjoining tissue as a result of MRI-induced heating and can take on critical values.

It is further preferred when the control unit is designed to switch the implantable medical device into an MRI operating mode in response to an output signal of the MRI detection unit that indicates an MRI-typical magnetic field and/or alternating electromagnetic field and/or mechanical vibrations, wherein the control unit is further designed to prompt a capturing of an impedance value characterizing an electrode-tissue contact in a recurring manner during the MRI operating mode, and to evaluate captured impedance values with respect to a change in the impedance value that indicates the formation of local edema. Such an implantable medical device can already detect potentially critical changes, and where applicable the formation of edema, during an MRI procedure and prompt suitable counter-measures where necessary, such as tissue cooling or termination of the MRI procedure. The latter can be done, for example, in that the implantable medical device emits control signals to a nuclear magnetic resonance tomograph or emits signals that can be perceived by operators of a nuclear magnetic resonance tomograph.

The control unit is further preferably designed to capture a discontinuation of an output signal of the MRI detection unit that indicates an MRI-typical magnetic field and/or alternating electromagnetic field and/or mechanical vibrations and to then terminate the MRI operating mode.

If a control unit is designed to record changes in the impedance value that indicate the formation of local edema, the control unit is further preferably designed to trigger edema-mitigating measures, in particular tissue cooling in the region of an electrode pole in question as soon as it has recorded changes in the impedance value that indicate the formation of local edema.

In any case, it is preferred for the implantable medical device to comprise a telemetry unit, which is connected and designed to transmit values of one or more system integration parameters to an external device. These values can then also be evaluated in a central service center and/or they can be further transmitted to the attending physician.

The telemetry unit is preferably connected to the control unit and designed to receive control commands from an external device, so that the implantable medical device can also be controlled by means of control commands from the outside, optionally also by remote control from a central service center, in a manner as is indicated by the recorded values of the system integrity parameters.

The test unit preferably comprises an impedance determination unit or is connected to such a unit. A series of values of system integrity parameters can be captured using such an impedance determination unit.

If the implantable electromedical device is a cardiac stimulator, which is designed to deliver stimulation pulses that can bring about a stimulated contraction of a ventricle, the test unit is preferably designed to carry out an automatic stimulation success check. Such an automatic stimulation success check is also known as automatic capture control (ACC) and can be carried out in a variety of ways, which are known per se, for example by way of impedance measurement.

BRIEF DESCRIPTION OF THE DRAWINGS

The invention will now be described in more detail based on embodiments with reference to the figures. In the drawings.

DETAILED DESCRIPTION OF THE INVENTION

Figure 1:
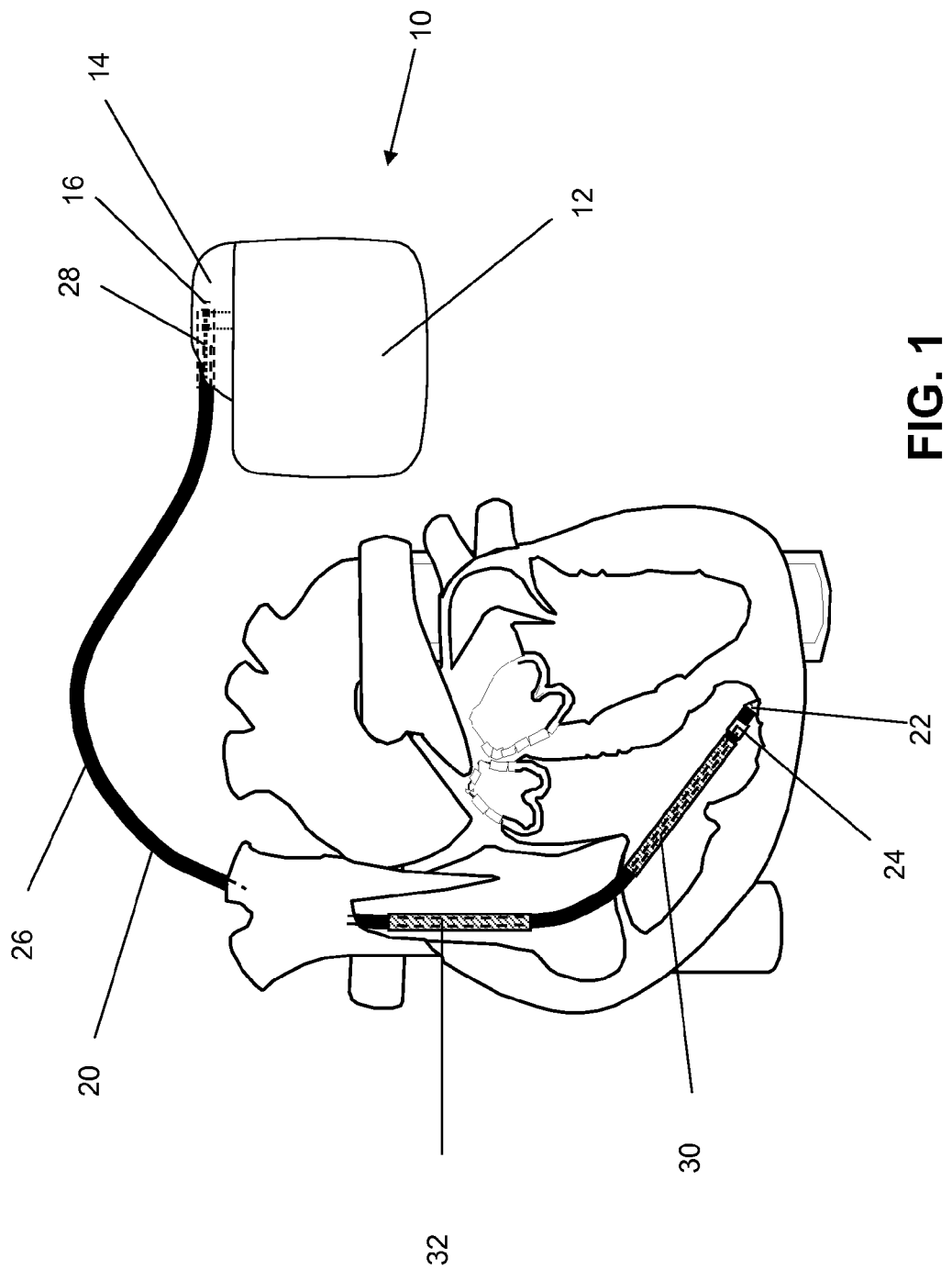
FIG. 1 shows an implantable cardiac stimulator 10 and an implantable electrode line 20 connected thereto as implantable medical devices.

FIG. 1 shows an implantable medical device in the form of an implantable cardiac stimulator 10, to which an electrode line 20 comprising an elongated conductor is connected.

The implantable cardiac stimulator 10 can be a cardiac pacemaker or a cardioverter/defibrillator (ICD). In the embodiment shown in FIG. 1, the cardiac stimulator 10 is a ventricular cardiac pacemaker and defibrillator. Other known cardiac stimulators are dual-chamber cardiac pacemakers for stimulating the right atrium and right ventricle, or biventricular cardiac pacemakers, which in addition to the right ventricle can also stimulate the left ventricle.

Such stimulators typically comprise a housing 12, which is generally made of metal and is therefore electrically conductive and can be used as a large-surface-area electrode pole. Typically, a terminal housing 14, which is also referred to as a header, is fastened to the outside of the housing 12. Such a header typically comprises contact bushings for receiving plug contacts. The contact bushings comprise electric contacts 16, which are connected to an electronics unit disposed in the housing 12 of the cardiac pacemaker 10 by way of corresponding conductors.

The electrode line 20 as defined by the present invention constitutes an implantable medical device having an elongated electric function conductor. Electrode poles in the form of a tip electrode 22 and an annular electrode 24 disposed in the vicinity of the tip electrode are disposed at a distal end of the electrode line 20 in the manner known per se. The electrode poles 22 and 24 are designed to be used, depending on the function of a cardiac stimulator to which the electrode line 20 is connected, for sensing electric potentials of the heart tissue (myocardium) or for delivering electric signals, for example for delivering stimulation pulses to the surrounding heart tissue. FIG. 1 shows how the electrode poles, these being the tip electrode 22 and the annular electrode 24, are located in the apex of a right ventricle of a heart when the electrode line 20 is used.

Both the tip electrode 22 and the annular electrode 24 are electrically connected to a contact of a connector 28 at the proximal end of the electrode line 20 by way of at least one electric conductor 26. The connector 28 comprises electric contacts, which correspond to the electric contacts 16 of the contact bushing in the terminal housing 14 of the implantable cardiac stimulator.

The electric conductors 26 in the electrode line 20 can be designed as approximately elongated sheathed cable conductors or helically coiled conductors. Such conductors, which connect the functional electrode poles to electric contacts of the plug contact at the proximal end of the electrode line 20 in an electrically conductive manner, are used to transmit electric signals from the plug contact to the respective electrode pole, or to conduct sensed signals representing electric potentials from the respective electrode pole to the plug contact.

The electric conductors 26, which connect the electrode poles 22 or 24 to the electric contact of the connector 28 of the electrode line 20, are surrounded by an insulating jacket over the majority of the lengths thereof, so that an electric contact with the tissue of the heart is specifically established by the electrode poles.

In addition to the electrode poles 22 and 24, which are typically used for the (in this case ventricular) stimulation of the heart tissue, the electrode line 20 also comprises two larger-surface-area electrode poles 30 and 32, which serve as defibrillation electrodes and are formed by at least one exposed helically coiled wire.

It should be pointed out that the invention, within the context of this embodiment, will be explained based on a right-ventricular cardiac pacemaker and defibrillator. However, any electromedical implant that is known per se, which is to say also a multi-chamber cardiac pacemaker or cardioverter/defibrillator (ICD), or a neurostimulator, or a pure monitoring implant, can be used as a medical device as defined by the invention.

Figure 2:
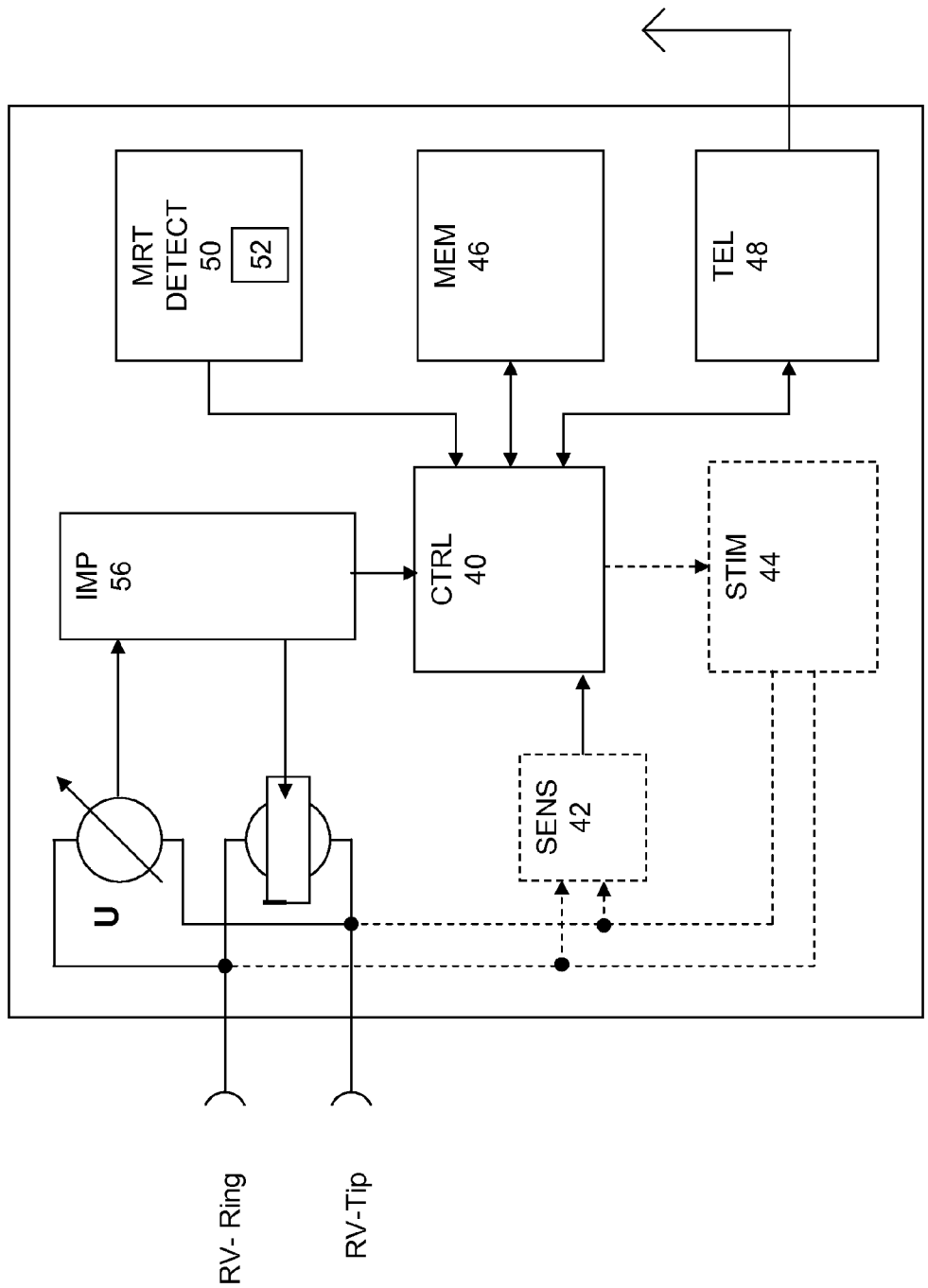
FIG. 2 shows, by way of example, several components of an implantable medical device according to an embodiment of the invention, as it is shown in FIG. 1, for example.

FIG. 2 is a schematic illustration, by way of example, of several components of the cardiac stimulator 10 from FIG. 1. Typical components of such a cardiac stimulator are a control unit 40, one or more sensing units 42, which each represent a diagnostic unit, and one or more stimulation units 44, which each represent a treatment unit. The control unit 40 is connected to both the sensing unit 42 and the stimulation unit 44. Both the sensing unit 42 and the stimulation unit 44 are connected to electrode terminals, respectively, so as to be able to capture electric potentials of the heart tissue by way of the right ventricular annular electrode 24 and/or the right ventricular tip electrode 22, in the case of the sensing unit 42, or so as to be able to deliver stimulation pulses, for example, by way of the right ventricular annular electrode 24 and/or the right ventricular tip electrode 22, in the case of the stimulation unit 44.

In addition, the control unit 40 is connected to a memory unit 46 for storing captured values of parameters to be measured. A telemetry unit 48, which is likewise connected to the control unit 40, allows captured values of parameters to be transmitted to an external device or control commands to be received from an external device.

The control unit 40 is additionally connected to an MRI detection unit 50, which is designed to detect MRI-typical magnetic fields and/or alternating electromagnetic fields and/or mechanical vibrations and to output an output signal to the control unit 40, the signal indicating the presence of such MRI-typical magnetic fields and/or alternating electromagnetic fields and/or mechanical vibrations. For this purpose, the MRI detection unit 50 comprises a magnetic field sensor 52 and/or sensors for detecting alternating electromagnetic fields and/or sensors for detecting mechanical vibrations.

The control unit 40 is additionally connected to a test unit in the form of an impedance determination unit 56. The impedance determination unit 56 is connected to a power source I and a voltage measuring unit U, which in turn are connected to the terminals for the annular electrode 24 and the tip electrode 22. In this way, the direct current source I can constantly deliver voltage pulses by way of the tip electrode 22 and the annular electrode 24 and the voltage measuring unit U can measure the respective voltage that is released. On the basis of these values, the impedance determination unit 56 can determine a particular impedance value.

An impedance value determined in this way depends on a variety of influencing variables. For example, a fracture of an electric conductor in the electrode line 20 would manifest itself in a very high impedance value. When the electrode line 20 is intact, the impedance to be measured between the electrode poles 22 and 24 also depends on the blood volume in the right ventricle of a heart, so that the impedance to be measured cyclically fluctuates in keeping with the cardiac cycle. For example, the impedance increases as the blood volume decreases, which is to say as the volume of the right ventricle decreases, so that a cyclical rise in the impedance indicates the cyclical contraction of the right ventricle. Likewise, a corresponding rise of the measured impedance due to ventricular contraction can indicate successful stimulation after delivery of a stimulation pulse. In this way, the impedance determination unit 56 is able to carry out automatic stimulation success control (automatic capture control (ACC)).

The impedance that is measured additionally depends on the impedance of the electrode pole-tissue contact. By evaluating the measured impedance values, it is therefore also possible to detect the formation of edema, which can occur, for example, by heating of the electrode poles due to alternating magnetic fields of a nuclear magnetic resonance tomograph.

Figure 3:
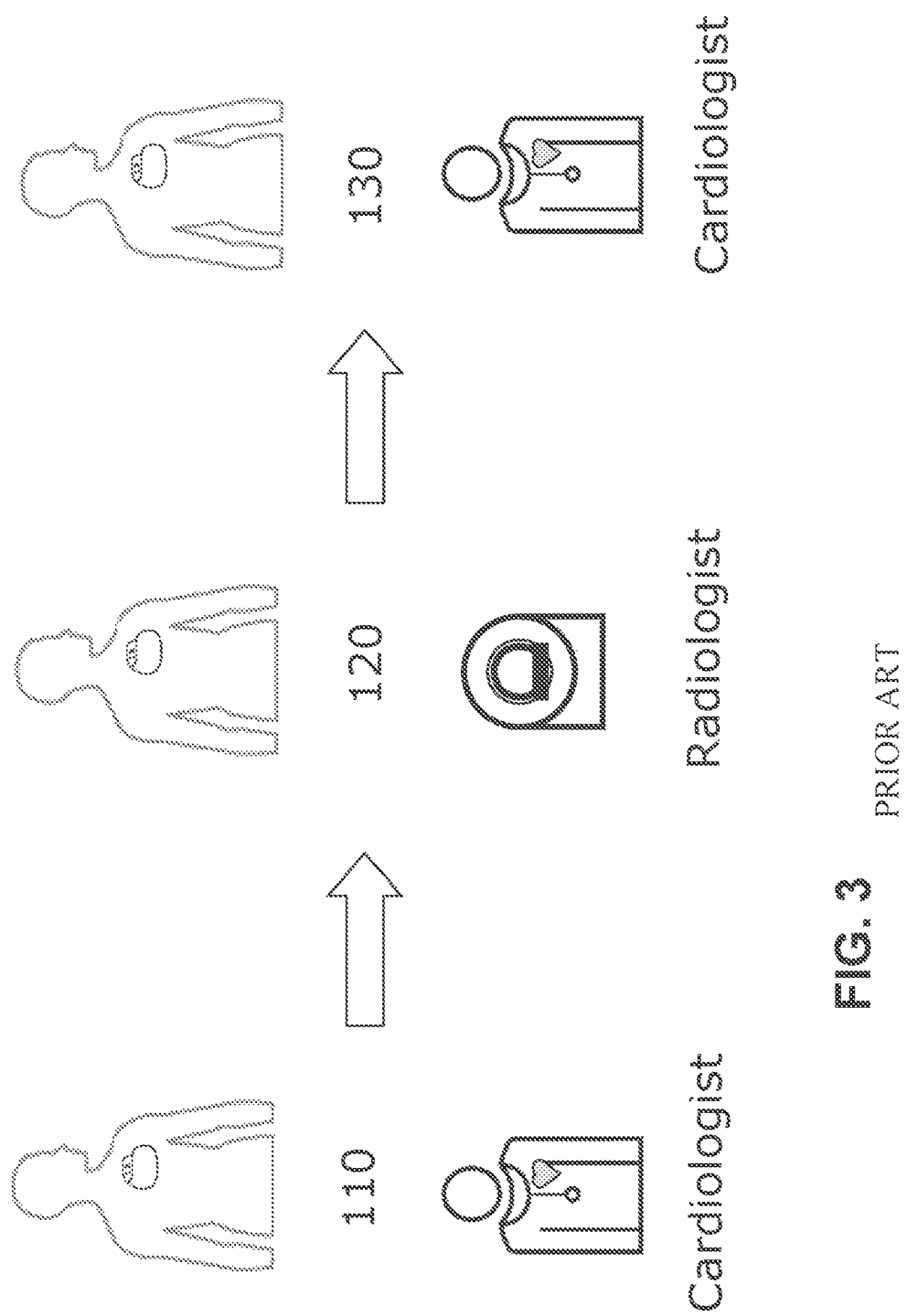
FIG. 3 explains the process of an MRI procedure as it is required according to the prior art.

FIG. 3 shows the presently required process of a prior and a follow-up check of an implantable medical device as is known in the art before and after an MRI procedure. A patient is examined at 110 by an implant specialist immediately before a planned MRI procedure. During this prior examination 110, the system integrity and electrode measurement values are captured for reference purposes so as to be able to compare them later to the results of the follow-up check. At this time, the implant may also be programmed to what is referred to as an MRI-safe mode.

Afterwards, the actual MRI procedure is carried out at 120 by the radiologist.

Immediately following the MRI examination, according to the applicable regulations the implant specialist must carry out a follow-up check at 130 of the implant system and evaluate the system integrity, for example by comparison with the initially determined values.

Compared to a "normal" MRI procedure, the overall procedure includes two additional procedures by an implant specialist and requires the implant specialist and radiologist to work closely with each other, both temporally and spatially, which in practical experience can only be implemented with considerably increased expenditure.

Figure 4:
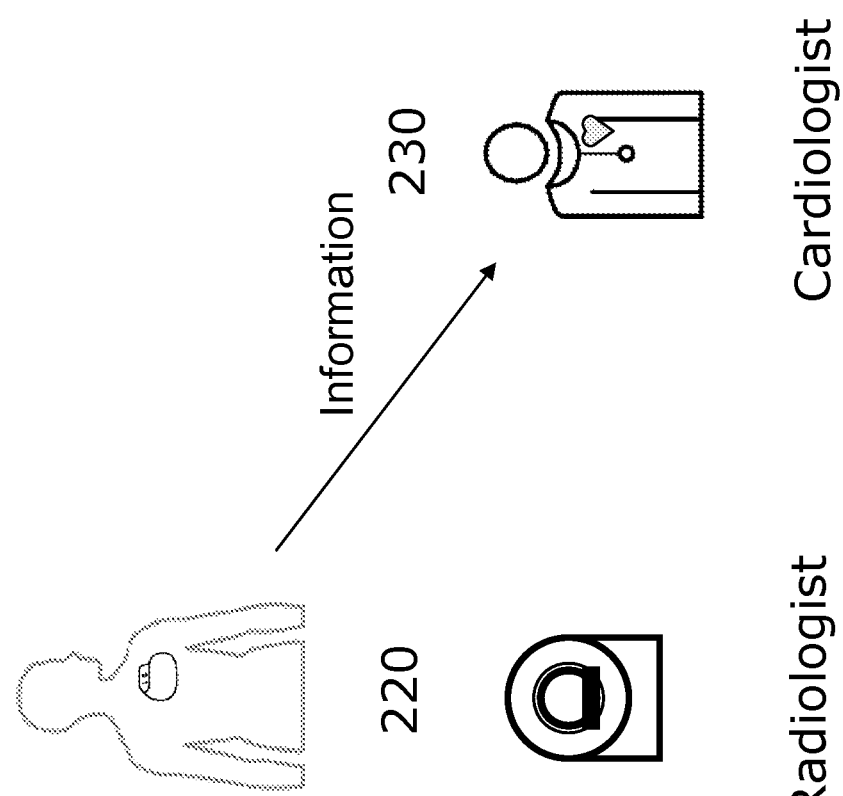
FIG. 4 shows the process of an MRI procedure using an implant according to an embodiment of the invention.

FIG. 4 shows the desired MRI procedure for a patient that has an electronic implant, thus showing the stated problem. Without a prior examination by the implant specialist, the patient can undergo an MRI examination (220), and the implant specialist (230) is automatically informed about the examination that has taken place and receives proof of the system integrity, without having to personally examine the patient. Compared to FIG. 3, embodiments of the invention improve the system integrity check additionally by further automatic ongoing checks.

The operating principle of the cardiac stimulator 10 or of another electronic implant implementing aspects of one or more embodiments of the invention is as follows:

If the electronic implant automatically detects an MRI environment (using, for example, a sensor as that which is described in the simultaneously pending application United States Patent Application Publication No. 20110152672), this triggers, with some predefined delay, automatic before-tests by capturing certain parameters, such as the stimulus threshold, electrode impedance, battery voltage, signal amplitudes, and the like. Thereafter, the attending implant specialist is automatically informed by a central service center that his patient had an MRI examination and thus receives, via remote data transmission, the data, which is to say the captured values of the system integrity parameters, which according to the present state of the art, the implant specialist would have had to collect personally.

If the MRI detection unit 50 recognizes an MRI, the control unit 40 immediately starts a "preliminary examination of the patient" as is customary according to current guidelines before an MRI examination. As part of such a before-test, for example electrode data such as impedance, stimulus threshold, signal amplitudes and the like are automatically determined and evaluated by the implant. If this test is not passed, the implant makes itself known to the MRI device—this being the nuclear magnetic resonance tomograph—using means such as those which are disclosed, for example, in the simultaneously pending application United States Patent Application Publication No. 20110152673, and the MRI procedure is aborted.

If the MRI detection unit 50 detects an MRI-typical magnetic field and/or alternating electromagnetic field and/or mechanical vibrations, the control unit 40 immediately triggers an MRI operating mode, and consequently an impedance monitoring process for characterizing the electrode-tissue contact so as to ascertain a potential formation of local edema, which may be the result of excessive heating or other irritation (by vibrations and the like) of the tissue. The control unit terminates the MRI operating mode, and thus the impedance monitoring process, after the "MRI end has been recognized" and sends the results to a central service center by means of the telemetry unit 48. When a threshold value for the captured impedance is exceeded, this is considered an indication of edema. This prompts the control unit to trigger a signal to the nuclear magnetic resonance tomograph and/or the control unit triggers mitigating measures, optionally while accepting higher energy consumption. Such mitigating measures can be, for example, active methods, such as cooling by means of a Peltier element (which then would likewise form part of the medical device). The recorded values of the system integrity parameters are also run to the Holter monitor so as to be read later, or if no wireless connection exists for wireless telemetry by way of the telemetry unit, or if the respective patient is not connected to a central service center.

An impedance measurement within the context of the determination of values of the system integrity parameters takes place in a frequency range of more than 100 kHz, excluding the bands of +/−5 MHz around the Larmor frequency typical of the respective MRI scanner. This prevents mutual interference, which is to say the scan sequence does not interfere with the impedance measurement of the implant, and conversely the impedance measurement of the implant does not interfere with imaging. In order to take into account different common MRI types (e.g. 1.5 T, 3 T, 7 T MRI) in the solution according to the invention, impedance measurements in the frequency ranges of 100 kHz-59 MHz, 69 MHz-123 MHz, 133 MHz-290 MHz, and >300 MHz are preferred. Other parameters to be monitored continuously or sporadically during an MRI procedure are, for example, monitoring of the stimulus threshold of the heart tissue. The stimulus threshold of the heart tissue indicates the intensity that a stimulation pulse must exceed to bring about a stimulated contraction of a particular ventricle. Within the context of a stimulus threshold test, typically stimulation pulses having different intensities are delivered to the heart tissue and thereafter a stimulation success check is carried out. In this way, the stimulation pulse intensity can be determined at which stimulation success occurs and the stimulus threshold of the respective heart tissue can be determined.

After an MRI examination detected by the MRI detection unit has been completed, the implant cyclically carries out ongoing checks of the system integrity parameters in a post-MRI operating mode and compares these to the parameters of the MRI examination and, in the event of a parameter drift following the MRI examination, notifies the implant specialist by way of telemetric data transmission to the central service center.

After an MRI examination detected by the MRI detection unit has been completed, the control unit 40 switches the implant into an "automatic post-MRI mode with automatic data transmission", wherein the values to be transmitted in the post-MRI mode are determined by a parameter comparison of the measured values before and after the MRI examination. The post-MRI mode is terminated either when the control unit 40 and/or the central service ascertain a "normalization" of the measured values of the system integrity parameters, which are monitored automatically by the implant in the further course, or by way of a remote programming command, which is triggered by the implant specialist via the central service center.

Figure 5:
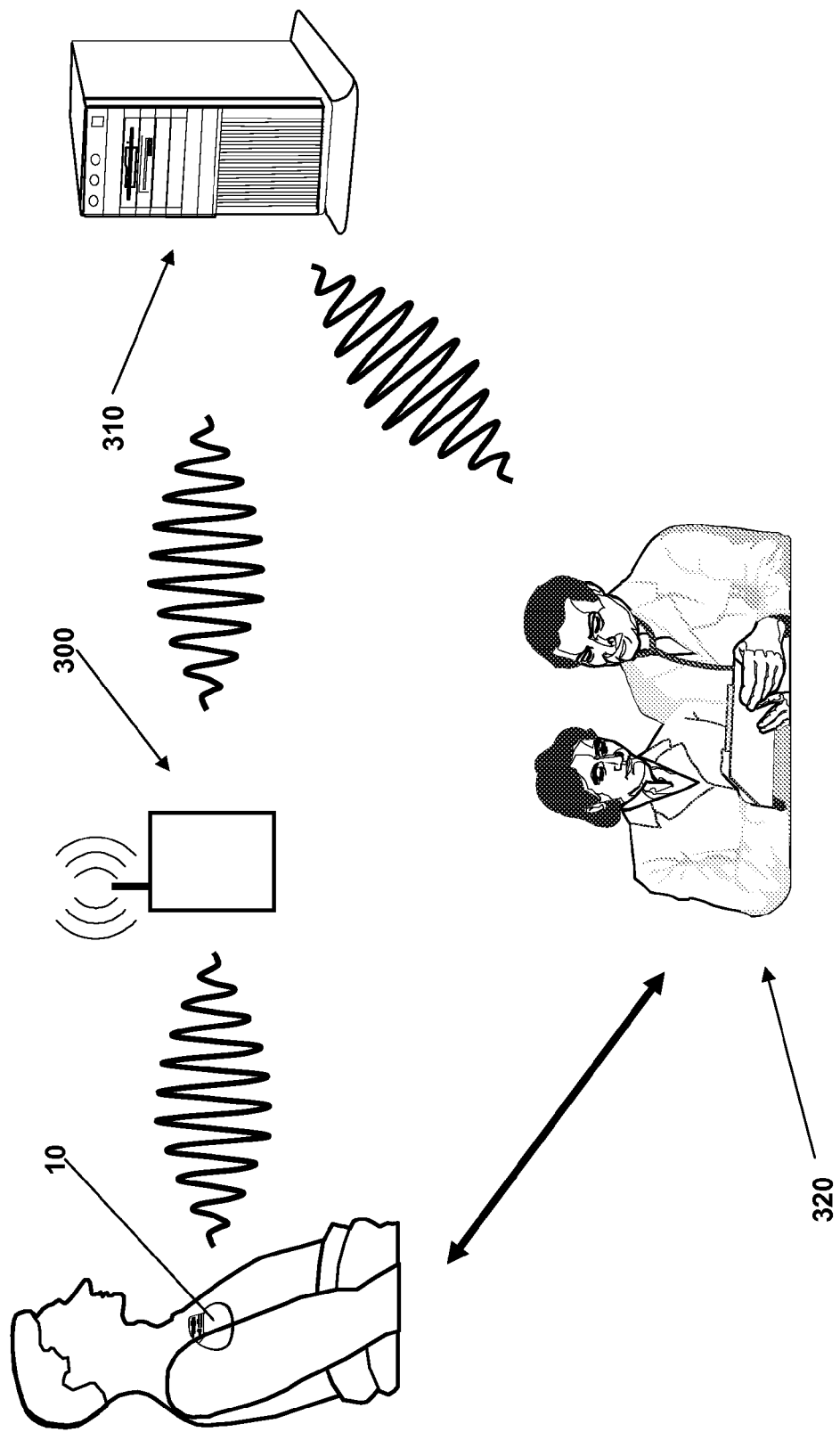
FIG. 5 shows how an implant 10 is connected telemetrically to a central service center 310 by way of a patient device 300 serving as a body-external relay station.

FIG. 5 shows how an implant 10 is connected telemetrically to a central service center 310 by way of a patient device 300 serving as a body-external relay station. Values received on the part of the implant 10 can be evaluated and assessed in the service center 310. The computing power available for this purpose is higher in the service center than in the implant. In addition, values of an implant can be compared to values of other similar or identical implants in the service center. By way of the central service center, it is also possible to notify the attending physician (cardiologist) or an implant specialist 320, who optionally can act on the implant 10 via the central service center or directly, for example if a need for appropriate action exists due to worsened values of system integrity parameters as a result of the MRI.

Embodiments of the invention described here for MRI-typical and similar magnetic field and/or alternating electromagnetic fields and/or mechanical vibrations can also be applied to other presently contraindicated treatment and diagnostic methods, such as therapeutic irradiation and the like. In this case, the MRI detection unit is replaced with another treatment detection unit that is geared to the respective diagnostic and/or treatment method.

In addition, alternating fields of a mechanical nature, such as vibrations or acoustic signals, are used, based on which the presence or absence of an interference field is recognized so as to switch to the described function modes of the implant based thereon.

The solution according to one or more embodiments of the invention has the advantage that it is possible to considerably simplify an MRI procedure for patients with electronic implants, without limiting patient safety as compared to the presently approved process.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable electromedical device, comprising
a detection unit configured to capture a device-impairing effect or effects;
a diagnostic-treatment unit configured to record physiological parameters or deliver a treatment or both record the physiological parameters and deliver the treatment, comprising
a diagnostic unit or
a treatment unit or
both the diagnostic unit and the treatment unit;
a memory;
a test unit configured to test the diagnostic-treatment unit, and to output test results obtained from said test and store said test results in said memory;
a control unit connected to the detection unit, the diagnostic-treatment unit, the memory and the test unit, wherein the control unit is configured to
actuate the test unit to test the diagnostic-treatment unit,
trigger a before-test of at least a portion of the diagnostic-treatment unit by the test unit in response to an output signal from said detection unit indicative of said device-impairing effect, wherein during the before-test, the test unit captures values of system integrity parameters that characterize an operating capability of the implantable medical device.

2. The implantable electromedical device according to claim 1, wherein the detection unit is a magnetic resonance imaging detection unit or an MRI detection unit configured to capture typical magnetic fields or alternating electromagnetic fields or mechanical vibrations or any combination thereof that are typical of an MRI.

3. The implantable electromedical device according to claim 2, wherein the control unit is configured to capture a discontinuation of said output signal of the MRI detection unit that indicates said typical magnetic fields or said alternating electromagnetic fields or said mechanical vibrations or said any combination thereof, and to then trigger the test unit to perform an after-test.

4. The implantable electromedical device according to claim 3, wherein the control unit is further configured to switch the implantable medical device, subsequent to said after-test, into a post-MRI operating mode, in which a plurality of after-tests are carried out cyclically, and compare values of a particular system integrity parameter from a particular after-test to a corresponding value of the particular system integrity parameter from a previous before-test and to terminate the post-MRI operating mode when the corresponding value is beneath a predefined threshold value.

5. An implantable electromedical device according to claim 1, wherein the implantable electromedical device is a stimulator or a monitoring implant having a tissue-contacting electrode pole, or a terminal configured to couple with a tissue-contacting electrode pole, and the system integrity parameters comprise an impedance value that indicates an electrode-tissue contact.

6. The implantable electromedical device according to claim 5, wherein the detection unit is a magnetic resonance imaging detection unit or an MRI detection unit configured to capture typical magnetic fields or alternating electromagnetic fields or mechanical vibrations or any combination thereof that are typical of an MRI and wherein the test unit is an impedance determination unit configured to obtain said impedance value and wherein the control unit is configured to switch the implantable medical device into an MRI operating mode in response to said output signal of the MRI detection unit that indicates said typical magnetic fields or said alternating electromagnetic fields or said mechanical vibrations or said any combination thereof, wherein the control unit is further configured to prompt said impedance determination unit to capture said impedance value to indicate an electrode-tissue contact in a recurring manner during the MRI operating mode, and to evaluate said impedance value with respect to detect critical changes in the impedance value.

7. The implantable electromedical device according to claim 6, wherein the control unit is configured to capture a discontinuation of said output signal of the MRI detection unit that indicates said typical magnetic fields or said alternating electromagnetic fields or said mechanical vibrations or said any combination thereof, and to then terminate the MRI operating mode.

8. The implantable electromedical device according to claim 6, wherein the control unit is configured to capture changes in the impedance value that indicate formation of a local edema and to then trigger an edema-mitigating measure.

9. The implantable electromedical device according to claim 8, wherein said edema-mitigating measure comprises tissue cooling.

10. An implantable electromedical device according to claim 1, wherein the implantable medical device comprises a telemetry unit, which is connected to said control unit and configured to transmit values from one or more of said system integration parameters to an external device.

11. The implantable electromedical device according to claim 10, wherein the telemetry unit is configured to receive control commands from the external device.

12. An implantable electromedical device according to claim 1, wherein the test unit comprises an impedance measurement unit or is connected to said impedance measurement unit.

13. The implantable electromedical device according to claim 12, wherein the impedance determination unit is configured to carry out an impedance measurement in a frequency range greater than 100 kHz and excludes frequency bands of +/−5 MHz around typical MRI Larmor frequencies.

14. An implantable electromedical device according to claim 1, wherein the implantable electromedical device is a cardiac stimulator, which is configured to deliver stimulation pulses configured to stimulate a contraction of a ventricle or a heart, and wherein the test unit is configured to carry out an automatic stimulation success check.

15. An implantable electromedical device, comprising
a detection unit configured to capture a device-impairing effect or effects;
wherein the detection unit is a magnetic resonance imaging detection unit or an MRI detection unit configured to capture typical magnetic fields or alternating electromagnetic fields or mechanical vibrations or any combination thereof that are typical of an MRI;
a diagnostic-treatment unit configured to record physiological parameters or deliver a treatment or both record the physiological parameters and deliver the treatment, comprising
a diagnostic unit or
a treatment unit or
both the diagnostic unit and the treatment unit;
a memory;
a test unit configured to test the diagnostic-treatment unit, and to output test results obtained from said test and store said test results in said memory;
a control unit connected to the detection unit, the diagnostic-treatment unit, the memory and the test unit, wherein the control unit is configured to
actuate the test unit to test the diagnostic-treatment unit,
trigger a before-test of at least a portion of the diagnostic-treatment unit by the test unit in response to an output signal from said detection unit indicative of said device-impairing effect, wherein during the before-test, the test unit captures values of system integrity parameters that characterize an operating capability of the implantable medical device;
wherein the control unit is configured to
capture a discontinuation of said output signal of the MRI detection unit that indicates said typical magnetic fields or said alternating electromagnetic fields or said mechanical vibrations or said any combination thereof, and to then trigger the test unit to perform an after-test,
switch the implantable medical device, subsequent to said after-test, into a post-MRI operating mode, in which a plurality of after-tests are carried out cyclically, and
compare values of a particular system integrity parameter from a particular after-test to a corresponding value of the particular system integrity parameter from a previous before-test and to terminate the post-MRI operating mode when the corresponding value is beneath a predefined threshold value.

* * * * *